United States Patent [19]

Hoskin

[11] Patent Number: 4,627,435
[45] Date of Patent: Dec. 9, 1986

[54] SURGICAL KNIVES

[75] Inventor: William J. Hoskin, Harpenden, United Kingdom

[73] Assignee: MICRA Limited, Luton, United Kingdom

[21] Appl. No.: 610,169

[22] Filed: May 14, 1984

[30] Foreign Application Priority Data

May 14, 1983 [GB] United Kingdom ................. 8313374

[51] Int. Cl.$^4$ ............................................. A61B 17/36
[52] U.S. Cl. ..................................... 128/303.1; 30/140; 219/233
[58] Field of Search ...................... 128/303.1; 219/233; 30/140; 433/32

[56] References Cited

U.S. PATENT DOCUMENTS 4,185,633 1/1980 Prozorov et al. ................. 128/303.1
4,209,017 6/1980 Shaw ................................. 128/303.1
4,273,127 6/1981 Auth et al. ........................ 128/303.1

FOREIGN PATENT DOCUMENTS 3107646 10/1982 Fed. Rep. of Germany ... 128/303.1
2071500 8/1981 United Kingdom ............. 128/303.1
2102678 2/1983 United Kingdom .

Primary Examiner—Lee S. Cohen
Attorney, Agent, or Firm—Sughrue, Mion, Zinn, Macpeak, and Seas

[57] ABSTRACT

A surgical knife includes a handle supporting a diamond blade. An Nd/YAG laser is optically coupled by a bundle of optical fibres to the blade. The arrangement enables the blade to cauterize tissue being incised by the knife. The selection of the material of the blade and the laser provides a laser knife of extended useful life. The heating of the diamond blade by the laser provides the blade with an unexpectedly increased cutting and cauterizing performance.

16 Claims, 6 Drawing Figures

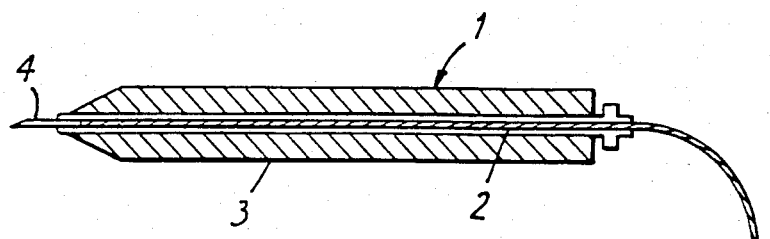
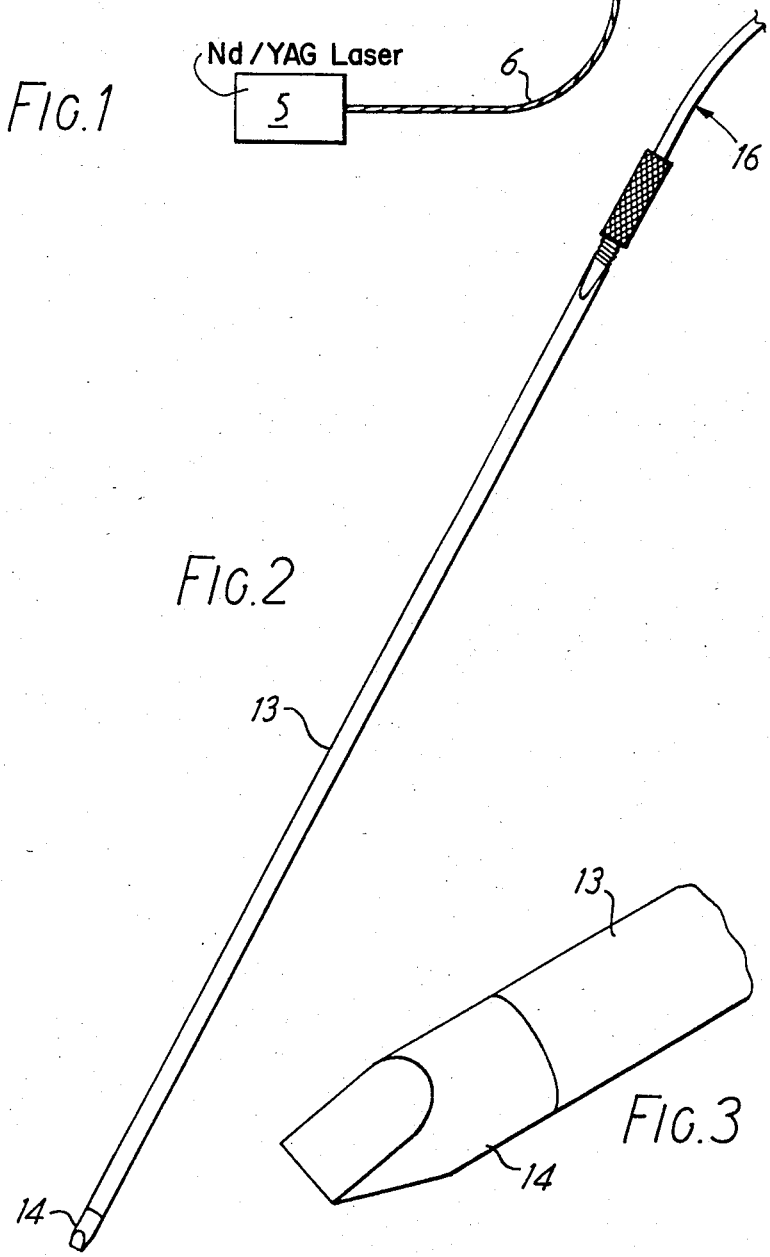
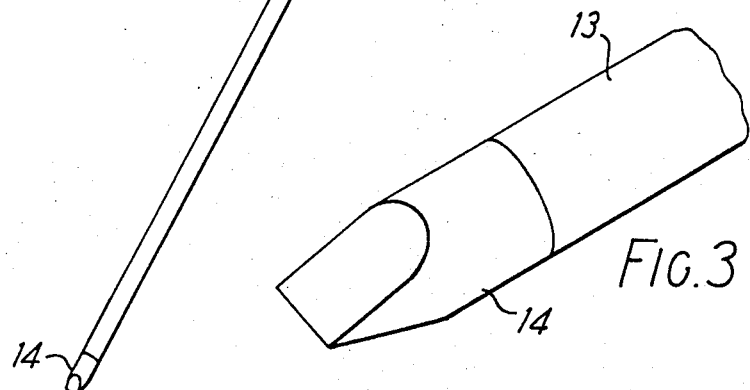

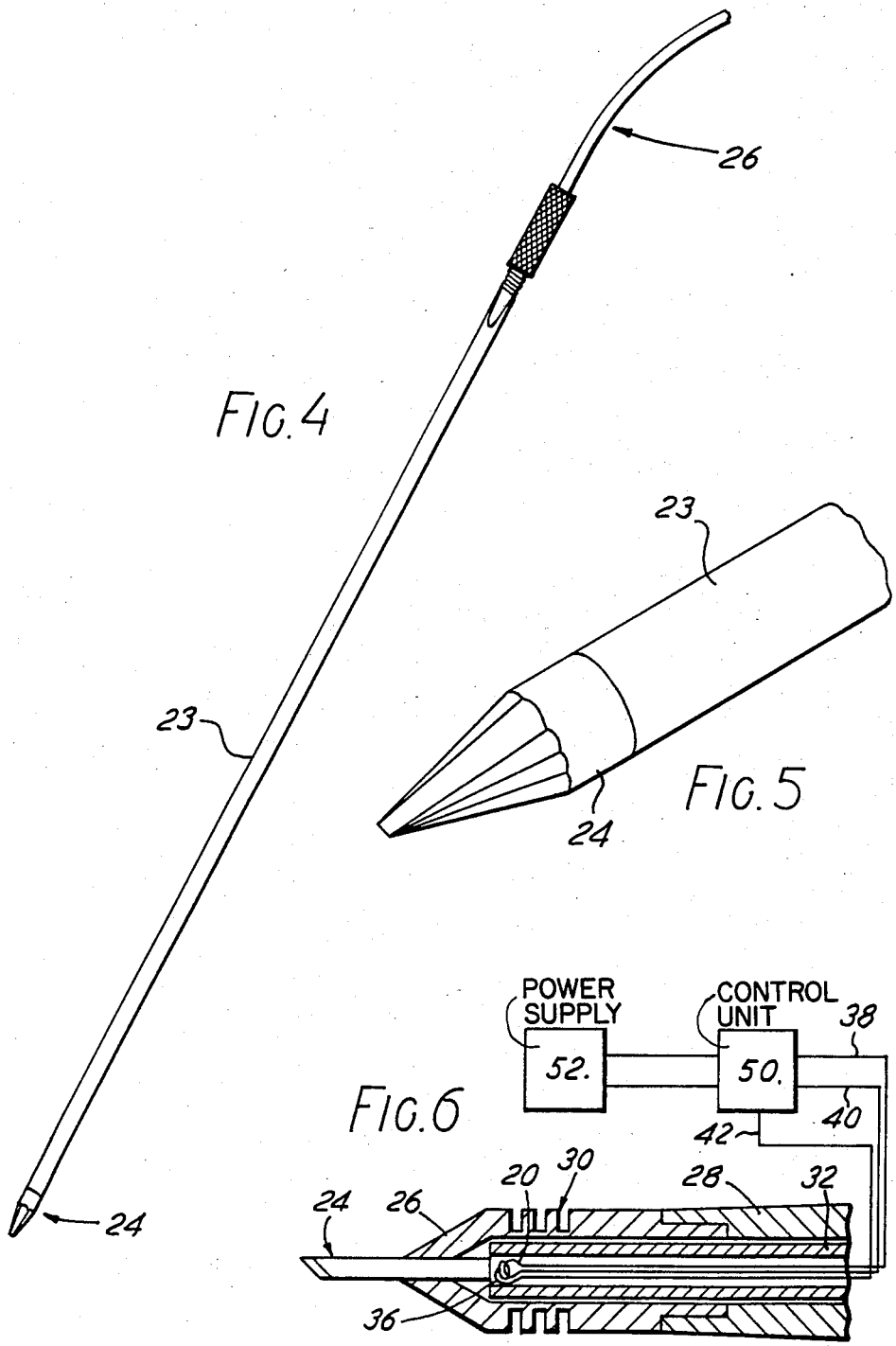

SURGICAL KNIVES

BACKGROUND OF THE INVENTION

1. Field of the Invention

The present invention relates to surgical knives.

2. Description of the Prior Art

Surgical scalpels have been proposed having a sapphire blade. An argon laser is coupled to the blade and energised to inject its high intensity light output into the immediately adjacent region of tissue being incised. The blue green light of the laser is selectively absorbed by the red haemoglobin of the blood in the walls of the incised tissue and rapid coagulation occurs to seal the walls of the incision.

A disadvantage of such scalpels is that the laser subjects the sapphire to thermal shock and these shocks promote cracks in the sapphire thereby reducing the life of the blade.

The solution to this problem has been to provide blades of softer material such as fused silica. However, while this has tended to extend the life of the blade with regard to cracking, blades of softer material wear more rapidly than harder materials and this in turn acts to limit the life of the blade.

Thus, it is an object of the invention to provide an improved surgical knife.

SUMMARY OF THE INVENTION

Accordingly, the invention provides a surgical knife comprising a diamond blade and means for heating the blade.

Accordingly, the invention further provides a knife comprising a diamond blade, a Neodymium/Yttrium Aluminium Garnet laser, and means optically coupling the radiation output from the laser to the vicinity of the cutting edge of the blade to enable the blade to cauterise tissue being incised by the knife.

BRIEF DESCRIPTION OF THE DRAWINGS

The invention may be further described, by way of example only, by reference to the accompanying diagrammatic drawings in which:

FIG. 1 is a plan view of a laser knife;

FIG. 2 is a perspective view of another form of laser knife;

FIG. 3 is a perspective view to an enlarged scale of the tip portion of the knife of FIG. 2;

FIG. 4 is a perspective view of yet another form of laser knife; and

FIG. 5 is a perspective view to an enlarged scale of the tip portion of the knife of FIG. 4; and FIG. 6 is a fragmentary section through still another form of surgical knife.

DESCRIPTION OF THE PREFERRED EMBODIMENTS

As shown in FIG. 1 a surgical diamond knife 1 has a handle 3 supporting a diamond blade 4. An optical fibre bundle 2 located within the handle 3 abuts an optically smooth surface of the diamond blade 4. A connector 6 couples the other end of the optical fibre bundle 2 to a radiation source in the form of a Neodymium/Yttrium Aluminium Garnet (Nd/YAG) Laser 5.

The ND/YAG laser 5 is in the form of a crystal pumped by means of a flash tube which provides a pulsed source of power.

To effect coagulation the laser is operated at a high peak power (e.g. 25-100 watts output), and either at a high repetition rate (e.g. at 1-10,000 pulses/second) or continuously.

With the above-described specific arrangement, i.e. the combination of the diamond blade and Nd/YAG laser, it has been found that the blade has a significantly longer life when compared with existing arrangements of radiation transmitting blades and lasers.

The laser knife of the present invention may, optionally, be combined with a conventional visible light source to cause the blade to luminesce (as disclosed in our published British Patent Application No. 8123635). This combination is particularly useful when the knife is used, e.g. in brain surgery where most incisions are made through small holes which may be deep and therefore dark.

The cauterising action of the blade is particularly valuable in removing cancerous tissue. When cutting away such tissue the surfaces being incised are speedily sealed against fluid loss as they are traversed by the cutting edge of the blade. The free flow of body fluids is thus prevented and the chances of recovery from the operation significantly improved.

It has also been found that using a Nd/YAG laser at its fundamental frequency it is possible to heat the diamond blade to quite high temperatures while, at the same time, achieving a certain amount of radiation from the cutting edge. At wavelengths which are absorbed by the diamond the heating of the blade results in a cauterising action taking place due to the heated blade closing blood vessels as it passes through them. This action is enhanced to some extent by the radiation of the laser energy from the blade itself. When arranged so that the greater part of the energy is used to heat the blade this in itself yields a cauterising action, even if little or no radiation is emitted.

The unusual property of the diamond is that it does not wet easily and does not easily stick to tissue and this is now apparent to a surprising extent. By increasing the temperature of the blade the situation can be reached where the blade is hot enough to cause cauterisation and yet, at the same time, the apparent coefficient friction of the blade is so much reduced that the ease by which the blade will cut is very much enhanced. This great increase in the cutting properties of the blade is of considerable importance as it can enable delicate cutting to be performed without distortion of the membrane being cut but, at the same time, blood vessels are sealed and a most effective way of excising a tumour is therefore achieved. The minimum temperature at which this effect occurs is quite critical. A temperature of at least 300° C. is necessary before the effect becomes apparent. The effect is maximised at a temperature of around 450° C. The lack of drag of the blade through the tissue is particularly apparent. If the blade is allowed to increase in temperature to some 600°-700° C. then the cutting edge deteriorates and it is important to control the temperature so that it does not exceed 550° C. For this purpose a small thermal-couple (not shown) is fitted to the diamond which can be used to control the laser or, alternatively, the natural property of the diamond itself (which can exhibit a variation of conductivity with temperature) can be used.

With malignant tumours, located for example in the lung, it has been found that if the energy from a Nd YAG laser can be directed into the centre of the tumour then the temperature of the tumour can be raised to 55°

C. By sustaining this temperature for a period of time the cancerous cells will be killed.

This treatment can be effected under local anaesthetic by using stiletto shaped diamond blades which can be directly pushed through the wall of the chest into the centre of the tumor.

The advantage of such treatment is that the resultant debris within the patient's chest can be coughed up by the patient leaving a clean scar and because only a local anaesthetic is required, the treatment can be conducted in environments outside an operating theatre, for example, in an out patient department.

Two different forms of knife particularly suiitable for such treatment of cancerous tissue are shown in FIGS. 2 and 3 and FIGS. 4 and 5.

The knife shown in FIGS. 2 and 3 has a handle 13 supporting a diamond blade 14. The handle 13 houses an optical fibre bundle (not shown) which is coupled at one end to the blade 14 and to a connector 16 at the other end.

The diamond blade 14 as shown more clearly in FIG. 3 has a cylindrical body portion 13 terminating in a wedge-shaped tip. The leading edge of the tip has a length substantially equal to the diameter of the cylindrical body portion.

The knife shown in FIGS. 4 and 5 has a handle 23 supporting a diamond blade 24. The handle 23 houses an optical fibre bundle (not shown) which is coupled at one end to the blade 24 and to a connector 26 at the other end.

The diamond blade 24 as shown in FIG. 5 has a cylindrical body portion and a profiled tip portion. The profiled tip portion has an axially extending central portion which is wedge-shaped and two axially extending lateral portions each of which defines part of a multi-sided cone. The leading edge of the wedge of the central portion extends between ¼ and 1/5 of the diameter of the body portion.

In a modification radiation from the laser may be coupled from the laser to the diamond blade by means of alternative methods such as those disclosed in co-pending application No. 81 23635 (Published Specification No. 2 102 678).

FIG. 6 shows a surgical knife having a diamond blade 24 which is heated by a resistance heating element 20. The high thermal conductivity of the diamond ensures that the heat is rapidly transferred from the heating element 20 to the cutting edge of the blade 24.

The blade 24 is held by a head 26 which is plugged into a socket of shank 28. The head 26 is provided with a plurality of cooling fins 30 which act as a thermal barrier against an excessive amount of heat being passed from the blade 24 to the shank 28.

The head 26 and the shank 28 which are both hollow, accommodate a tube 32 supporting the heating element 20, a thermocouple 36 contacting a central portion of the heating element 20, and electrical conductors 38, 40 and 42 which provide the means for connecting the heating element and the thermocouple to a control unit 50 and a power supply 52.

In operation power is supplied from the power supply 52 in pulsed form through the control unit 50 to the heating element 20. The temperature of the heating element is thus varied by varying the mark space ratio of the pulses supplied. The signal generated by the thermocouple 36 is used to control the mark space ratio of the pulses in a sense to maintain the temperature of the heating element and therefore that of the diamond blade at a substantially constant 500° C.

With the blade heated to this level it has been found to possess unexpected beneficial properties. For example a considerable reduction in friction between the blade and the tissue being cut was found to occur as well as a significant degree of cauterisation.

It will be appreciated that the diamond blade can be heated by means other than a laser or a heating element.

Many modifications can be made to the invention without departing from the scope and spirit of the invention as defined in the appended claims.

I claim:

1. A surgical knife comprising:
a diamond blade,
a holder mounting said blade, and
means carried by said holder and coupled to the blade for heating the blade.

2. A surgical knife according to claim 1, further including
temperature control means responsive to the heating means for controlling the temperature of the knife to lie within a predetermined range.

3. A surgical knife according to claim 2 wherein said range is from 300° to 550° C.

4. A surgical knife according to claim 2, wherein said heating means comprises a resistance heating element and means for connecting said resistance heating element to a source of electrical power.

5. A surgical knife according to claim 4, wherein said temperature control means comprises a thermocouple connected to the heating element to provide an electrical output signal as an indication of the temperature of the heating element, and means responsive to said electrical signal for controlling current flow from said source of electrical power to said heating element.

6. A surgical knife according to claim 5, wherein the control means comprises means connected to said source of electrical power for supplying current pulses to said heating element, and a control unit connected between the supply means and the heating element to vary the mark space ratio of said pulses in dependence upon the level of the output signal from the thermocouple.

7. A surgical knife according to claim 1, wherein said heating means comprises a laser and said knife includes means for connecting said laser to a source of electrical power, and means for optically coupling the radiation output of said laser to said blade.

8. A surgical knife according to claim 7 wherein the laser comprises a Neodymium/Yttrium Aluminium Garnet laser.

9. A surgical knife according to claim 1, wherein said holder includes a shank and said shank includes a thermal barrier for limiting the transfer of heat from the blade and said heating means along the shank of the knife.

10. A knife according to claim 1 wherein the blade is stiletto-shaped to enable the blade to be directly introduced into the central portion of a cancerous tumour within the body of a patient.

11. A knife according to claim 1 wherein the blade comprises a cylindrical body portion and a wedge-shaped tip portion.

12. A knife according to claim 11 wherein the leading edge of the tip portion is substantially equal in length to the diameter of the body portion.

13. A knife according to claim 11 wherein the length of the leading edge of the tip portion is substantially in the range of from ¼ to 1/5 of the diameter of the body portion.

14. A surgical knife comprising:
a diamond blade,
a holder mounting said blade,
a Neodymium/Yttrium Aluminum Garnet laser, and
means carried by said holder for optically coupling the radiation output from the laser to the vicinity of the cutting edge of the blade, to enable the blade to cauterise tissue being incised by the knife.

15. A knife according to claim 14, wherein said blade includes an optically smooth surface and the optically coupling means comprises a bundle of optical fibres extending from said optically smooth surface of the diamond blade to the laser.

16. A knife according to claim 15, wherein said holder comprises a handle supporting the diamond blade and through which said bundle of optical fibers pass.

* * * * *